US008389235B2

(12) United States Patent
Ohmori et al.

(10) Patent No.: US 8,389,235 B2
(45) Date of Patent: Mar. 5, 2013

(54) METHODS FOR SPECIFICALLY SELECTING ANTIBODY-PRODUCING CELLS

(75) Inventors: Hitoshi Ohmori, Okayama (JP); Naoki Kanayama, Okayama (JP)

(73) Assignee: Hitoshi Ohmori, Okayama (JP)

( * ) Notice: Subject to any disclaimer, the term of this patent is extended or adjusted under 35 U.S.C. 154(b) by 455 days.

(21) Appl. No.: 12/064,324

(22) PCT Filed: Aug. 29, 2006

(86) PCT No.: PCT/JP2006/316904
§ 371 (c)(1),
(2), (4) Date: Jun. 5, 2008

(87) PCT Pub. No.: WO2007/026661
PCT Pub. Date: Mar. 8, 2007

(65) Prior Publication Data
US 2008/0227123 A1    Sep. 18, 2008

(51) Int. Cl.
C12P 21/06    (2006.01)
C12N 5/00     (2006.01)
C12N 15/63    (2006.01)

(52) U.S. Cl. ............................................. 435/69.1

(58) Field of Classification Search ............... None
See application file for complete search history.

(56) References Cited

U.S. PATENT DOCUMENTS

| 2005/0026246 A1 | 2/2005 | Sale et al. |
| 2005/0059082 A1 | 3/2005 | Breitling et al. |
| 2006/0183225 A1 | 8/2006 | Ohta et al. |
| 2008/0193979 A1 | 8/2008 | Sale et al. |
| 2010/0093033 A1 * | 4/2010 | Maizels et al. ............... 435/69.1 |

FOREIGN PATENT DOCUMENTS

| JP | 2005-503826 A | 2/2005 |
| JP | 2005-507241 A | 3/2005 |
| JP | 2006-109711 A | 4/2006 |
| WO | WO 02/100998 A2 | 12/2002 |
| WO | WO 2004/011644 A1 | 2/2004 |

OTHER PUBLICATIONS

Kanayama, N., et al., "Reversible switching of immunoglobulin hypermutation machinery in a chicken B cell line," *Biochemical and Biophysical Research Communications*, vol. 327(1), pp. 70-75 (Feb. 4, 2005).

Kanayama, N., et al., "Genetic manipulation of an exogenous non-immunoglobulin protein by gene conversion machinery in a chicken B cell line," *Nucleic Acids Research*, vol. 34(2), e10, 9 pgs (Jan. 18, 2006).

Li, X., et al., "Inactivation of the SR protein splicing factor ASF/SF2 results in genomic instability," *Cell*, vol. 122(3), pp. 365-378 (Aug. 12, 2005).

Liu, X., et al., "Exonic splicing enhancer-dependent selection of the bovine papillomavirus type 1 nucleotide 3225 3' splice site can be rescued in a cell lacking splicing factor ASF/SF2 through activation of the phosphatidylinositol 3-kinase/Akt pathway," *Journal of Virology*, vol. 77(3), pp. 2105-2115 (Feb. 2003).

Seo, H., et al., "Rapid generation of specific antibodies by enhanced homologous recombination," *Nature Biotechnology*, vol. 23(6), pp. 731-735 (Jun. 2005, Epub May 29, 2005).

PCT International Preliminary Report on Patentability (Chapter I) issued for PCT/JP2006/316904 on Mar. 13, 2008, 6 pgs.

Hudson, P., et al., "Engineered antibodies," *Nature Medicine*, vol. 9(1), pp. 129-134, (Jan. 2003).

Todo, K., et al., "Novel In Vitro Screening System for Monoclonal Antibodies Using Hypermutating Chicken B Cell Library," *Journal of Bioscience and Bioengineering*, vol. 102(5), pp. 478-481 (Nov. 2006).

Wang, J., et al., "Targeted disruption of an essential vertebrate gene: ASF/SF2 is required for cell viability," *Genes Div.*, vol. 10(20), pp. 2588-2599 (Oct. 15, 1996).

Winding, P., et al., "The chicken B cell line DT40: a novel tool for gene disruption experiments," *Journal of Immunological Methods*, vol. 249(1-2), pp. 1-16 (Mar. 1, 2001).

Cumbers, S.J., et al., "Generation and iterative affinity maturation of antibodies in vitro using hypermutating B-cell lines," *Nat. Biotechnol.*, vol. 20, pp. 1129-1134 (2002).

Todo, K., et al., Protein evolution system using a chicken B cell line; switching on and off of mutation machinery, *Seikagaku*, vol. 76(8), p. 992, 3P-688 (2004).

U.S. Appl. No. 13/510,910, which is a U.S. National Stage of PCT/JP2010/006759 filed on Nov. 18, 2010, 122 pages.

* cited by examiner

*Primary Examiner* — Michail Belyavskyi
(74) *Attorney, Agent, or Firm* — Kilpatrick Townsend & Stockton LLP

(57) ABSTRACT

Methods are provided for selecting B cells that produce a desired antibody, comprising a step of culturing B cells, which have the properties of cell death being induced under specific conditions and that cell death being suppressed by a signal generated as a result of the binding between an antigen and an antibody expressed on B cell surface (B cell antigen receptor on the B cell surface), with an antigen under conditions in which cell death is induced, and selecting antibody-producing B cells that bind with the antigen as viable cells.

16 Claims, 10 Drawing Sheets

METHODS FOR SPECIFICALLY SELECTING ANTIBODY-PRODUCING CELLS

CROSS-REFERENCES TO RELATED APPLICATIONS

This application is a U.S. National Stage Application of PCT/JP2006/316904, filed Aug. 29, 2006, which claims the benefit of Japanese Application No. 2005-247074, filed Aug. 29, 2005.

TECHNICAL FIELD

The present invention relates to methods for efficiently screening and isolating antibody-producing cells using cultured cells.

BACKGROUND ART

Conventional antibody production methods typically consisted of immunizing an animal to obtain polyclonal antibodies from serum, or alternatively, immunizing a mouse or rat, isolating antibody-producing cells and obtaining monoclonal antibodies from a hybridoma established by cell fusion with a myeloma. Since these methods use live animals, the procedures are complicated and require considerable time and cost.

On the other hand, DT40 cells—a chicken B cell line—spontaneously cause mutation of antibody genes during culture and produce a diverse antibody repertoire.

Although there are reports on cells that produce antibodies having the desired specificity through physical adsorption onto an antigen obtained from a DT40 cell group during culture (see, for example, Patent Document 1, Patent Document 2 and Non-Patent Document 1), the accuracy of this method is low and requires considerable time and cost, similar to conventional methods.

Since the chicken B cell line DT40 and certain types of human or mouse B cell lines retain the ability to spontaneously cause mutation of their antibody genes during culture, a diverse repertoire of antibody genes is accumulated in such cultured cell populations. If it were possible to efficiently screen for B cells expressing a desired antibody from among these cells, it would be possible to establish an efficient antibody production method that uses cultured cells rather than animals. Such a method would become an important fundamental technology for producing antibodies in vitro.

In vitro antibody production methods are superior in that they are able to overcome several inevitable restrictions placed on in vivo antibody production methods using living organisms. For example, although it is difficult to obtain antibodies to self components, or to produce antibodies by immunizing with highly toxic antigens with in vivo production systems, these can be accomplished with in vitro systems.

Since the incidence of cells producing a desired antibody is predicted to be extremely low in the cultured B cells used in the present invention, it is virtually impossible to take out the individual cells and test their antibody production ability. Typically, the method referred to as "panning", in which an antigen is immobilized onto a certain type of support and cells bound to the support are separated from unbound cells, or methods using a cell sorter are used to separate cells. However, to take out the less frequently occurring cells, the selection has to be performed repeatedly requiring both time and labor while the success rate is not necessarily high.

[Patent Document 1] Japanese Patent Kohyo Publication No. (JP-A) 2005-503826 (unexamined Japanese national phase publication corresponding to a non-Japanese international publication)
[Patent Document 2] Japanese Patent Kohyo Publication No. (JP-A) 2005-507241 (unexamined Japanese national phase publication corresponding to a non-Japanese international publication)
[Non-Patent Document 1] Cumbers, S. J. et al., Nature Biotechnology, 20:1129-1134 (2002)
[Non-Patent Document 2] Liu, X. et al., Journal of Virology, 77:2105-2115 (2003)
[Non-Patent Document 3] Li, X., Manley, J. L., Cell, 122: 365-378 (2005)

DISCLOSURE OF THE INVENTION

Problems to be Solved by the Invention

An objective of the present invention is to provide methods for efficiently producing and isolating antibody-producing cells using cultured cells, comprising culturing antibody-producing cells under conditions in which only those cells that produce a desired antibody survive.

Means for Solving the Problems

DT40 cells—a chicken B cell line—spontaneously mutate their antibody genes during culture and produce a diverse antibody repertoire. If it were possible to isolate a clone that produces a desired antibody from among the cells producing a diverse range of antibodies, then this method could be used as an efficient antibody production technology.

It is extremely difficult to rigorously screen for a small number of cells producing a desired antibody from among a vast number of cells by, for example, physical adsorption to an antigen. In contrast, the present inventors aimed to establish a positive selection method by which only those cells that produce a desired antibody survive, while unnecessary cells die off. Although this type of positive selection process actually proceeds in the living body, there have been no examples so far of the realization of a similar process in cultured cells.

The present inventors adopted a basic strategy for establishing a positive selection method, which includes producing DT40 cells introduced with a lethal mutation that causes cell death when placed under certain culture conditions, and establishing conditions by which a survival signal is transmitted to cells, which signal allows the cells to survive when an antigen binds to an antibody expressed on the cell surface (B cell antigen receptor, abbreviated as BCR), but causes death to cells to which the antigen did not bind.

Based on this approach, the present inventors conducted studies on DT40 cell lines having various lethal mutations, and as a result, surprisingly found that positive selection is possible in a DT40 cell line with a mutated alternative splicing factor (ASF) (referred to as DT40-ASF).

In this DT40-ASF, one of the native ASF alleles of DT40 is deactivated by targeted gene disruption. The other allele is substituted with a human ASF (hASF) gene positioned downstream of a promoter having a Tet operator sequence. When DT40-ASF is cultured with tetracycline, or its analogoue doxycycline (Dox), expression of hASF is terminated, which then causes cell death due to a splicing abnormality or DNA instability. This fact demonstrates that the expression of ASF gene is required for cell survival. In addition, the present inventors surprisingly found that cell death of DT40-ASF in the presence of Dox is suppressed by the binding between BCR and the antigen. Based on this finding, when DT40-ASF cells were cultured in the presence of Dox after having added an arbitrary antigen, cells expressing BCR specific to that antigen were confirmed to survive preferentially. Therefore, positive selection of an antigen-specific DT40 clone was determined to be possible according to this principle. Thus, the present inventors found that, if a "means" capable of terminating the expression of various genes essential for survival by any form of external stimulus without being limited to ASF, is introduced into a B cell line, and cell death induced by terminating that gene expression can be suppressed by a survival signal from a BCR, then any gene can be used for positive selection, thus completing the present invention.

In other words, the present invention relates to the following embodiments:

[1] a method for selecting B cells that produce a desired antibody, comprising the step of culturing B cells, which have the properties of:
cell death being induced under specific conditions, and
cell death being suppressed by a signal generated by binding between an antigen and
an antibody expressed on B cell surface (B cell antigen receptor on B cell surface), with an antigen under conditions in which cell death is induced, and selecting antibody-producing B cells that bind with the antigen as viable cells;

[2] a method for selecting B cells that produce a desired antibody, comprising the step of culturing B cells,
in which cell death is induced by terminating the expression of a specific gene essential for survival, and
which have the property of cell death being suppressed by a signal generated by binding between an antigen and an antibody expressed on B cell surface (B cell antigen receptor on B cell surface),
with an antigen under conditions in which cell death is induced by termination the expression of the specific gene, and selecting antibody-producing B cells that bind with the antigen as viable cells;

[3] a method for selecting B cells that produce a desired antibody, comprising the step of culturing B cells,
in which a specific endogenous gene essential for survival has been functionally disrupted,
which are introduced with a gene construct in which an exogenous gene having the same function as the specific gene and a promoter are operably linked, and
which have the property of cell death induced by terminated expression of the exogenous gene being suppressed by a signal generated as a result of binding between an antigen and an antibody expressed on B cell surface (B cell antigen receptor on the B cell surface),
with an antigen under conditions in which cell death is induced by termination the activity of the promoter, and selecting antibody-producing B cells that bind with the antigen as viable cells;

[4] a method for selecting B cells that produce a desired antibody, comprising the step of culturing B cells,
in which a specific endogenous gene essential for survival has been functionally disrupted, which is introduced with a gene construct in which a promoter whose activity is induced by an external stimulus, and an exogenous gene having the same function as the specific gene are operably linked, and
which have the property of cell death being induced by terminated expression of the exogenous gene being suppressed by a signal generated as a result of binding between an antigen and an antibody expressed on B cell surface (B cell antigen receptor on the B cell surface),
with an antigen under conditions in which cell death is induced due to the absence of an external stimulus, and selecting antibody-producing B cells that bind with the antigen as viable cells;

[5] a method for selecting B cells that produce a desired antibody, comprising the step of culturing B cells,
in which a specific endogenous gene essential for survival has been functionally disrupted,
which is introduced with a gene construct in which a promoter whose activity terminates by an external stimulus, and an exogenous gene having the same function as the specific gene are operably linked,
and which have the property of cell death being induced by terminated expression of the exogenous gene being suppressed by a signal generated as a result of binding between an antigen and an antibody expressed on B cell surface (B cell antigen receptor on the B cell surface),
with an antigen under conditions in which cell death is induced by an external stimulus and selecting antibody-producing B cells that bind with the antigen as viable cells;

[6] a method for selecting B cells that produce a desired antibody, comprising the step of culturing B cells,
in which an endogenous ASF gene has been functionally disrupted,
which is introduced with the following gene constructs (a) and (b),
  (a) a gene construct in which a promoter having a Tet operator sequence and an exogenous ASF gene are operably linked; and
  (b) a gene construct in which a promoter and a DNA encoding a transcription activating factor having a Tet repressor domain are operably linked,
and which have the property of cell death being induced by terminated expression of an exogenous ASF gene that is suppressed by a signal generated as a result of the binding between an antigen and an antibody expressed on B cell surface (B cell antigen receptor on B cell surface),
with an antigen under conditions in which cell death is induced by tetracycline or an analog thereof, and selecting antibody-producing B cells that bind with the antigen as viable cells;

[7] a method for selecting B cells that produce a desired antibody, comprising the step of culturing B cells described below with an antigen under conditions in which cell death is induced by tetracycline or an analog thereof, and selecting antibody-producing B cells that bind with the antigen as viable cells:
B cells in which one of the endogenous ASF gene loci is substituted with a gene construct containing a promoter having a Tet operator sequence operably linked to an exogenous ASF gene, while the other ASF gene loci is substituted with a gene construct containing a promoter operably linked to a DNA encoding a transcription activating factor having a Tet repressor domain, and which have the property of cell death induced by terminated expression of the exogenous ASF gene being suppressed by a signal generated as a result of binding between an antigen and an antibody expressed on B cell surface (B cell antigen receptor on the B cell surface);

[8] a method for selecting B cells that produce a desired antibody, comprising the step of culturing B cells described below with an antigen under conditions in which cell death is induced by tetracycline or an analog thereof, and selecting antibody-producing B cells that bind with the antigen as viable cells:

B cells in which expression of an exogenous Cre recombinase gene is induced by an extracellular stimulus, and expression of activation-induced cytidine deaminase (AID) can be induced or terminated as a result of the invertion of orientation of exogenous AID gene by the expressed Cre recombinase, which B cells have the characteristics of:
  (i) having a functionally disrupted endogenous AID gene, and thus AID protein produced as a result of endogenous AID gene expression is not produced;
  (ii) have an exogenous AID gene sandwiched between two loxP sequences in mutually opposite directions, and a promoter able to function in the cells is present upstream of the domain sandwiched by the two loxP sequences, in which promoter-mediated expression of AID gene is possible when the AID gene is located in the forward direction relative to the promoter, while expression of AID gene is terminated when the AID gene is located in the reverse direction relative to the promoter; and
  (iii) Cre recombinase gene is introduced in a manner that enables activation of Cre recombinase by an extracellular stimulus, and the direction of the domain sandwiched between the two loxP domains containing the exogenous AID gene is reversed,
wherein one of the loci of endogenous ASF gene is substituted with a gene construct containing a promoter having a Tet operator sequence operably linked to an exogenous ASF gene, while the other ASF gene loci is substituted with a gene construct containing a promoter operably linked to a DNA encoding a transcription activating factor having a Tet repressor domain, and having the property of cell death being induced by terminated expression of the exogenous ASF gene being suppressed by a signal generated as a result of the binding between an antigen and an antibody expressed on B cell surface (B cell antigen receptor on the B cell surface);

[9] a method for selecting B cells that produce a desired antibody, comprising the step of culturing B cells, which are introduced with a gene construct containing a promoter of a gene of which its transcription is activated by a signal generated by the binding between an antigen and an antibody expressed on B cell surface (B cell antigen receptor on B the cell surface), which promoter is operably linked to a drug resistance gene, with an antigen under conditions in which cell death is induced by the drug, and selecting antibody-producing B cells that bind with the antigen as viable cells;

[10] the method of [9], wherein the gene whose transcription is activated by a signal generated as a result of the binding between an antigen and an antibody expressed on B cell surface (B cell antigen receptor on the B cell surface) is NFκB gene or IκB gene;

[11] the method of any one of [1] to [10], wherein the B cells are from a chicken B cell line;

[12] the method of any one of [1] to [10], wherein the B cells are from the chicken B cell line DT40;

[13] the method of any one of [6] to [8], wherein the B cells are from the chicken B cell line DT40, and the exogenous ASF gene is a human ASF gene;

[14] a method for obtaining a desired antibody, comprising the steps of:
  (i) selecting B cells producing a desired antibody according to the method of any one of [1] to [13]; and
  (ii) obtaining the antibody from the selected B cells;

[15] an antibody obtained according to the method of [14];

[16] a variant of the antibody obtained according to the method of [14];

[17] a B cell in which one of the loci of endogenous ASF gene is substituted with a gene construct containing a promoter having a Tet operator sequence operably linked to an exogenous ASF gene, while the other ASF gene loci is substituted with a gene construct containing a promoter operably linked to a DNA encoding a transcription activating factor having a Tet repressor domain;

[18] a B cell in which expression of an exogenous Cre recombinase gene is induced by an extracellular stimulus, and expression of activation-induced cytidine deaminase (AID) can be induced or terminated as a result of inversion of orientation of exogenous AID gene by the expressed Cre recombinase, these B cells having the characteristics of:
  (i) have a functionally disrupted endogenous AID gene, and thus the AID protein produced as a result of endogenous AID gene expression is not produced;
  (ii) have an exogenous AID gene sandwiched between two loxP sequences in mutually opposite directions, and a promoter able to function in the cells is present upstream of the domain sandwiched by the two loxP sequences, in which promoter-mediated expression of AID gene is possible when the AID gene is located in the forward direction relative to the promoter, while expression of AID gene is terminated when the AID gene is located in the reverse direction relative to the promoter; and
  (iii) Cre recombinase gene is introduced in a manner that enables activation of Cre recombinase by an extracellular stimulus, and the direction of the domain sandwiched between the two loxP domains containing the exogenous AID gene is reversed,
wherein one of the loci of endogenous ASF gene is substituted with a gene construct containing a promoter having a Tet operator sequence operably linked to an exogenous ASF gene, while the other ASF gene loci is substituted with a gene construct containing a promoter operably linked to a DNA encoding a transcription activating factor having a Tet repressor domain;

[19] the cell of [17] or [18], wherein the B cell is from a chicken B cell line;

[20] the B cell of [17] or [18], wherein the B cell is from the chicken B cell line DT40; and

[21] the B cell of [17] or [18], wherein the B cell is from the chicken B cell line DT40 and the exogenous ASF gene is a human ASF gene.

BRIEF DESCRIPTION OF THE DRAWINGS

FIG. 4 shows an overview of a method for positively selecting high-affinity antibody-producing B cells utilizing ASF mutation together with the structure of DT40-ASF cells. In FIG. 4B, the vertical bars represent doxycycline (Dox), the open circle inside the diagram of a B cell represents the tetR-VP16 transcription factor, and the open circle/vertical bar represents the tetR-VP16 transcription factor bound to doxycycline (DOX), as described in Example 3.

BEST MODE FOR CARRYING OUT THE INVENTION

Method for Selecting Antigen-Specific Antibody-Producing B Cells

Figure 1:
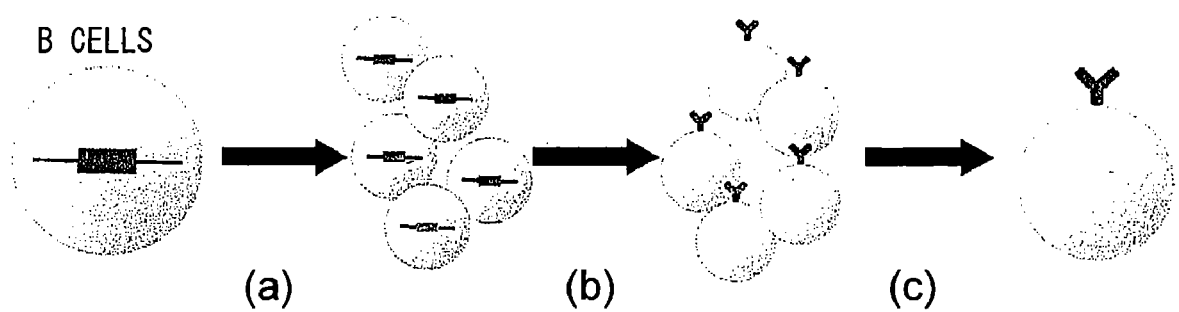
FIG. 1 shows an overview of the production of high-affinity antibodies by diversification and selection of B cells resulting from antibody gene mutation. (a) diversification due to mutation in antibody variable region gene; (b) B cells expressing antibody molecules on its surface; (c) Selection of B cells expressing high-affinity antibodies.
Figure 2:
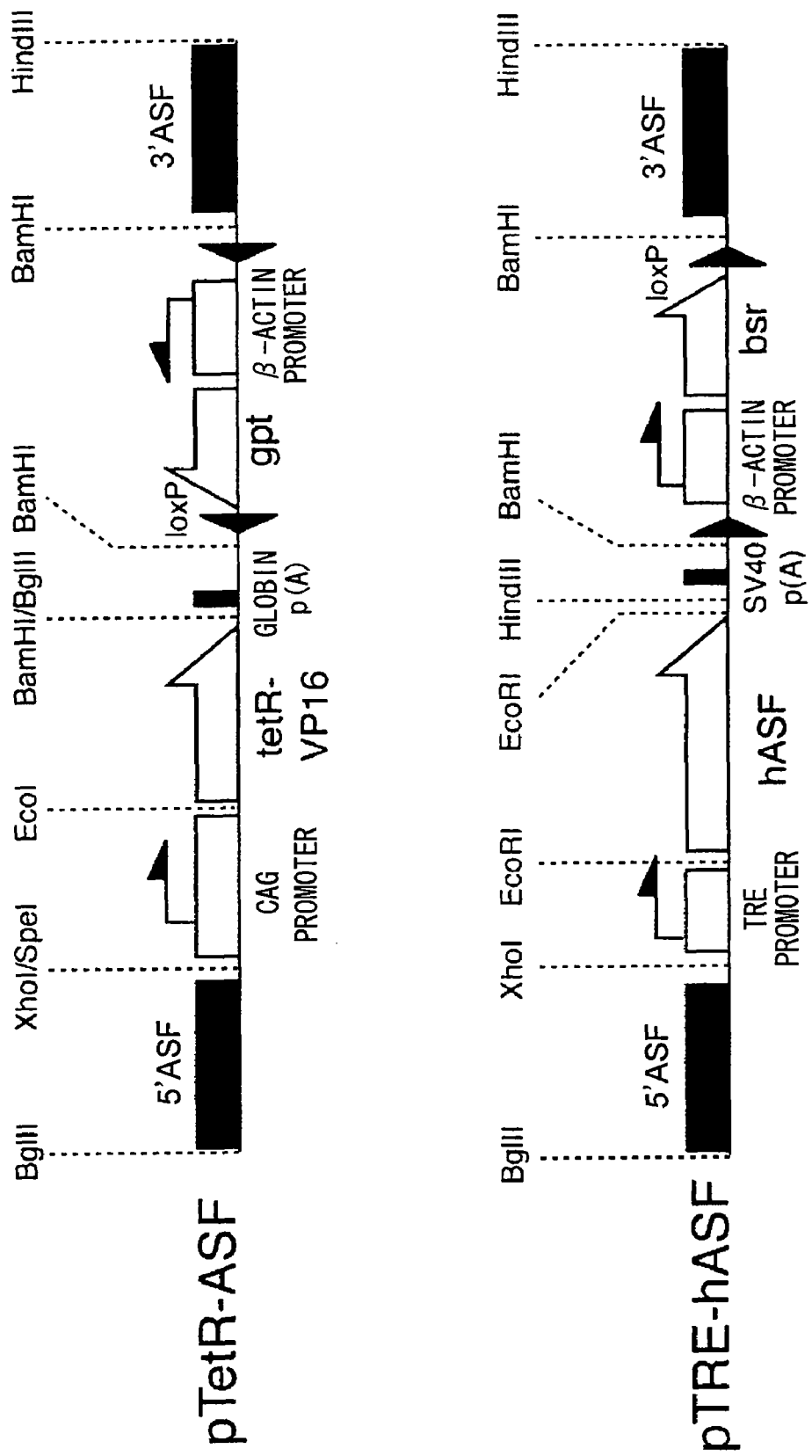
FIG. 2 shows a diagram of gene constructs used to prepare DT40 capable of controlling expression of ASF.

The process by which the immune system produces antibodies having high affinity for an antigen (high-affinity antibodies) proceeds as follows. As shown in FIG. 1, mutations are introduced at a high frequency into antibody variable region genes of B cells stimulated with an antigen, and a cell population that expresses a diverse range of antibody genes is formed. Since rigorous selection is carried out on this population in which only those B cells that express a high-affinity antibody survive while other cells die, the antibodies produced have an increased affinity.

The present invention reproduces the above process using a cultured B cell line, enabling antibodies to be efficiently produced without having to carry out an immunization procedure using animals.

In the present invention, there are no limitations on the source of animal species or the type of cell line, so long as the cultured B cells used are able to produce an antibody. For example, human, mouse, sheep, rat, rabbit or chicken B cells or cell lines thereof can be used. Preferably, Ramos cell lines derived from human Burkitt's lymphoma or DT40 cell lines derived from chicken B cells can be used, and most preferably, DT40 cell lines can be used.

DT40 cells spontaneously cause mutation of their antibody genes during culture, resulting in the cell population forming a diverse antibody repertoire. In addition, due to the high frequency of targeted homologous recombination due to introduced exogenous genes, DT40 cells also offer a valuable advantage that facilitates genetic manipulation of the cells. Thus, the establishment of a technology for efficiently and selectively isolating cells expressing a desired antibody from a population of DT40 cells would be beneficial in terms of constructing an antibody production system that uses cultured cells.

In the methods of the present invention, a positive selection method is adopted for screening and isolating desired antibody-producing cells of interest which occur at a low frequency. This method comprises culturing a cell population under culture conditions in which only cells of interest producing a desired antibody survive while all other cells die.

A positive selection method refers to a method in which, conditions are set such that survival signals are transmitted into cells enabling them to survive when an antigen binds to an antibody expressed on the surface of B cells (B cell antigen receptor, abbreviated as BCR), while cells to which antigens are not bound die. Culturing B cells with an antigen under such conditions allow selection of live B cells that produce an antibody that binds with the antigen.

Namely, the present invention provides a method for selecting B cells that produce a desired antibody, comprising the step of culturing B cells having the properties of (i) cell death being induced under specific conditions, and (ii) cell death being suppressed by a signal generated as a result of binding between an antigen and an antibody expressed on B cell surface (B cell antigen receptor on B cell surface: BCR), with an antigen under cell death-inducing conditions, and selecting antibody-producing B cells that bind with the antigen as viable cells.

In other words, the above method can be expressed as a method for selecting B cells that produce a desired antibody, comprising the step of culturing B cells having the properties of (i) cell death being induced under specific conditions, and (ii) cell death being suppressed by a signal generated as a result of binding between an antigen and an antibody expressed on B cell surface (B cell antigen receptor on B cell surface: BCR), with an antigen under cell death-inducing conditions, which is also a method for selecting antibody-producing B cells that bind with the antigen as viable cells.

Here, "the binding between an antigen and an antibody expressed on B cell surface (B cell antigen receptor on B cell surface: BCR)" refers to binding between an antigen and an antibody that recognizes that antigen and is expressed on B cell surface (B cell antigen receptor on B cell surface: BCR), or non-specific binding between an antigen and an antibody expressed on the surface of B cells (B cell antigen receptor on B cell surface: BCR).

An antigen of the present invention is not limited to a known substance, and all kinds of substances are included.

BCR is a trigger of a biochemical cascade of B cell activation that induces proliferation and differentiation of B cells. BCR utilizes an Igα and Igβ immune receptor tyrosine-based activation motif (ITAMs) to activate non-receptor-type protein tyrosine kinases (PTKs). PTKs belonging to three different classes (Src-PTKs, Syk, Btk) are known to be involved in the control of the signal transduction pathway downstream of BCR. A survival signal is transmitted into cells through pathways such as the PI3-kinase/Akt pathway via BCR. Survival signals from the BCR are able to suppress abnormalities in DNA stability such as cleavage or relocation of DNA occurring due to gene abnormalities essential for survival such as splicing factors and the like.

Since B cells expressing BCR that bind with a specific antigen on the cell surface are able to produce an antibody to that antigen, antibody-producing cells that produce a desired antibody can be obtained by isolating those B cells. In the present invention, it is important to set conditions for inducing cell death that are antagonized by the survival signal from the BCR.

For this, B cells introduced with a lethal mutation that causes death when subjected to certain culture conditions are cultured under those conditions, together with an antigen of the desired antibody. For example, although cell death may be induced by terminating the expression of a specific gene, B cells, which have been introduced with a gene construct (also referred to as a DNA construct) that contains a gene through which cell death caused by terminating the expression of a specific gene is suppressed by a signal generated by the binding between a B cell antigen receptor on B cell surface and an antigen, are cultured in the presence of an antigen against a desired antibody under conditions that allow only those cells expressing a B cell antigen receptor against that antigen on its cell surface to survive. More specifically, B cells, in which cell death is induced by terminating the expression of a specific gene essential for survival, and which have the property of cell death being suppressed by a signal generated as a result of binding between an antigen and an antibody expressed on B cell surface (B cell antigen receptor on B cell surface: BCR), are cultured with an antigen of the desired antibody under conditions in which cell death is induced by terminating the expression of that specific gene. More specifically, B cells in which a specific endogenous gene essential for survival has been functionally disrupted and which have been introduced with a gene construct in which a promoter and an exogenous gene having the same function as the specific gene is operably linked, and which have the property of cell death that is induced by terminating expression of that exogenous gene being suppressed by a signal generated as a result of the binding between an antigen and an antibody expressed on B cell surface (B cell antigen receptor on the B cell surface: BCR), are cultured together with an antigen of a desired antibody under conditions in which cell death is induced by terminating the activity of that promoter.

Various cells can be used for the B cells introduced with the gene construct as described above, such as B cells introduced with a gene construct containing genes whose expression is terminated due to an external stimulus. Examples of such B cells include B cells in which a specific endogenous gene that is essential for survival is functionally disrupted, and which have been introduced with a gene construct in which a promoter whose activity is induced by an external stimulus is operably linked to an exogenous gene having the same function as the specific gene. B cells introduced with such a gene construct and which have a suppressive property on cell death induced by terminating the functioning of the exogenous gene, due to the binding between an antigen and an antibody expressed on B cell surface (B cell antigen receptor on the B cell surface: BCR), are cultured with an antigen for a desired antibody under conditions in which cell death is induced due to the absence of the external stimulus.

In the present invention, "operably linked" refers to the binding of a gene or DNA downstream of a promoter so that expression of the gene or DNA is induced as a result of a transcription factor binding to the promoter. In addition, in the present invention, an "exogenous gene having the same function as the specific gene" refers to, for example, a gene same as the specific gene or a gene homologous to the specific gene. In addition, examples of an "exogenous gene having the same function as the specific gene" include a gene derived from a species same as the biological species from which the specific gene is derived, or from a different species. In addition, in the present invention, the "termination" or "suppression" of the promoter activity and the "termination" or "suppression" of gene expression not only refers to the complete termination or suppression thereof, but also includes an incomplete termination or suppression as long as cell death is induced by that termination or suppression.

In addition, examples of B cells introduced with a gene construct containing a gene whose expression is terminated by an external stimulus, include B cells in which a specific endogenous gene essential for survival is functionally disrupted, and which have been introduced with a gene construct in which a promoter whose activity is interrupted by an external stimulus is operably linked to an exogenous gene having the same function as the specific gene. B cells introduced with such a gene construct, and having a suppressive property on cell death induced by terminating the expression of the exogenous gene that is suppressed by a signal generated as a result of the binding between an antigen and an antibody expressed on B cell surface (B cell antigen receptor on the B cell surface: BCR), are cultured with an antigen for a desired antibody under conditions in which cell death is induced by an external stimulus.

Cell death of these cells can be suppressed by the transmission of a survival signal into cells when a B cell antigen receptor of cells that express, on their cell surface, a B cell antigen receptor against the above-described antigen binds with the antigen. Namely, only those B cells that express the B cell antigen receptor that binds with the specific antigen can survive. Such cells are B cells capable of producing an antibody against the specific antigen.

An example of a gene essential for survival is alternative splicing factor (ASF). B cells having a lethal mutation in an alternative splicing factor may thus be used. Both endogenous ASF genes are deactivated by substitution using targeted homologous recombination by using an ASF gene construct having a mutation that causes loss of function. Any such mutation can be used for the ASF gene mutation so long as it causes a loss of function, and methods such as the insertion of a drug resistance gene such as Neo into an ASF gene or insertion of a translation stop codon can be used. Any B cell line may be used for the introduction of the mutation as long as it retains the ability to spontaneously cause mutation of an antibody gene; however, chicken B cell line DT40 is preferably used due to its high homologous recombination frequency.

ASF of any biological species may be used for an exogenous ASF introduced in place of a disrupted endogenous ASF whose expression is controllable by an external stimulus so long as it is able to take over the splicing function of the endogenous ASF. Various promoters and the like that are capable of terminating the function of ASF in response to an extracellular stimulus can be used to control exogenous ASF expression. Examples of promoters that can be used include, but are not limited to, promoters whose activity is suppressed in the presence of a drug (drug-suppressed promoters), such as promoters whose activity is suppressed in the presence of tetracycline (tetracycline-suppressed promoters). When a drug-suppressed promoter is used, the drug serves as the external stimulus. In addition, promoters of a type that expresses ASF in the presence of an extracellular stimulus but terminates ASF expression when the stimulus is removed can also be used. An expression controlled type ASF gene may be introduced into either one of the endogenous ASF gene locus sites or a site outside the ASF gene locus.

Culture conditions during the culturing of cells that produce antibodies, the amount of external stimulus (such as drugs) added, and such, can be suitably determined by a person skilled in the art.

Figure 4A:
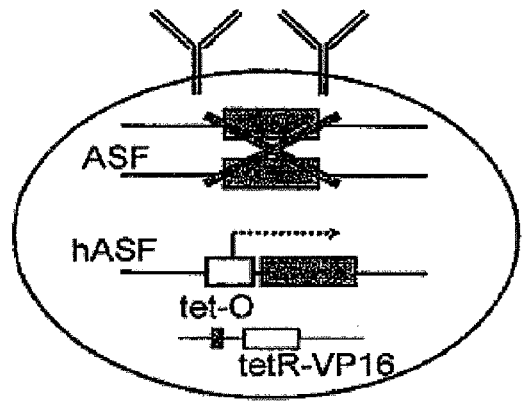
FIG. 4A (labeled Prior Art) shows the DT40-ASF cell described in Wang, J., Takagaki, Y. and Manley, J. L., Genes Dev., 10:2588-2599 (1996).
Figure 4B:
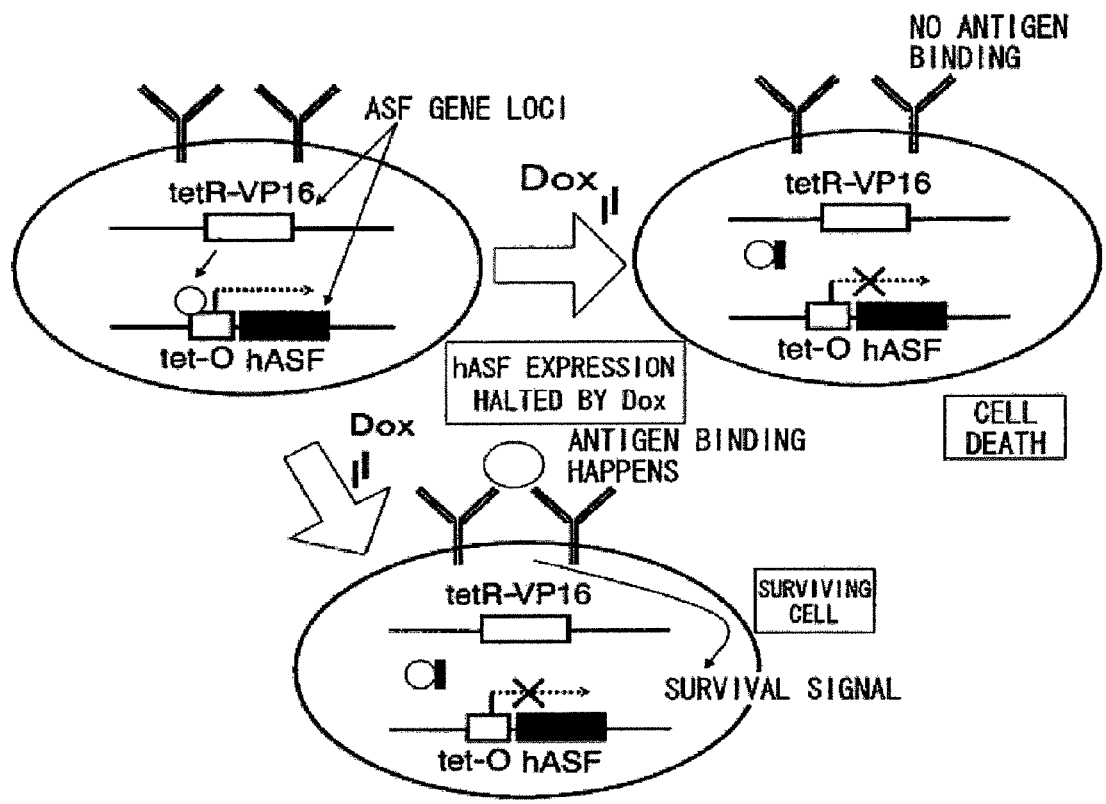
FIG. 4B shows the DT40-ASF cell produced by the inventors of the present invention.

DT40-ASF cell lines can be produced according to the method described in Wang, J., Takagaki, Y. and Manley, J. L., Genes Dev., 10:2588-2599 (1996) (FIG. 4A). In addition, these cell lines can also be produced using the method described in Example 3 to be described later (FIG. 4B). Moreover, the DT-40-SW-ASF cell lines described in Example 3 to be described later can also be used.

As shown in FIG. 4A, in the DT40-ASF produced according to the method described in Wang, J., Takagaki, Y. and Manley, J. L., Genes Dev., 10:2588-2599 (1996), both of the original ASF alleles present in DT40 are deactivated by targeted gene disruption. Since cells are unable to survive in this state due to abnormal RNA splicing, a human ASF (hASF) gene located downstream of a promoter having a Tet operator sequence and a tetR-VP16-expressing construct are additionally introduced. However, since gene introduction in this case is the result of non-specific transfection, the introduction site is not specified.

Since expression of hASF terminates when DT40-ASF is cultured in the presence of tetracycline, or its analog doxycycline (Dox), cells die due to a splicing abnormality. This fact indicates that expression of ASF gene is essential for cell survival. In the DT40-ASF produced by the present inventors, one of the ASF alleles originally present in DT40 is deactivated by substituting it with a tetR-VP16-expression construct. The other allele is substituted with a human ASF (hASF) gene located downstream of a promoter having a Tet operator sequence (FIG. 4B). The DT40-ASF produced by the present inventors can be produced in fewer steps than the DT40-ASF produced according to the method described in Wang, J., Takagaki, Y. and Manley, J. L., Genes Dev., 10:2588-2599 (1996).

Cell death of DT40-ASF in the presence of Dox is avoided by a signal generated as a result of the binding between the BCR and antigen. Thus, if a gene construct capable of terminating ASF gene expression essential for survival due to an external stimulus is introduced into a B cell line, and the cells are cultured in the presence of an antigen under conditions such that ASF expression is terminated, conditions can be set to such that after a certain amount of time, only those cells bound to antigens survive, while other cells die (see FIG. 4).

Namely, the present invention provides a method for selecting B cells that produce a desired antibody comprising the following steps:
a step in which the following gene constructs (a) and (b) are introduced into B cells having a functional disruption of endogenous ASF genes:
  (a) a gene construct in which a promoter having a Tet operator sequence and an exogenous ASF gene are operably linked; and
  (b) a gene construct in which a promoter and a DNA encoding a transcription activating factor having a Tet repressor domain are operably linked,
a step where B cells, which have the property of cell death, which is induced by terminating the expression of an exogenous ASF gene, being suppressed by a signal generated as a result of the binding between an antigen and an antibody expressed on B cell surface (B cell antigen receptor on the B cell surface), are cultured with an antigen under conditions in which cell death is induced by tetracycline or an analog thereof, and selecting B cells that produce an antibody that binds with the antigen as viable cells.

There are no particular limitations on the tetracycline analogs of the present invention so long as they can be used in the methods of the present invention. Examples include doxycycline (Dox), oxytetracycline, dimethylchlorotetracycline and minocycline.

Examples of B cells introduced with the aforementioned gene constructs include, but are not limited to, B cells in which one of the endogenous ASF gene loci is substituted with a gene construct containing a promoter having a Tet operator sequence operably linked to an exogenous ASF gene, while the other endogenous ASF gene loci is substituted with a gene construct containing a promoter operably linked to a DNA encoding a transcription activating factor having a Tet repressor domain.

In addition, examples of B cells introduced with the aforementioned gene constructs include, but are not limited to, B cells in which (a) expression of an exogenous Cre recombinase gene is induced by an extracellular stimulus, (b) expression of activation-induced cytidine deaminase (AID) can be induced and terminated as a result of inversion of exogenous AID gene orientation by the expressed Cre recombinase, and (c) the following characteristics are present:
(1) have a functionally disrupted endogenous AID gene, and thus the AID protein produced as a result of endogenous AID gene expression is not produced;
(2) have an exogenous AID gene sandwiched between two loxP sequences in mutually opposite directions, and a promoter able to function in the cells is present upstream of the domain sandwiched by the two loxP sequences, in which promoter-mediated expression of AID gene is possible when the AID gene is located in the forward direction relative to the promoter, while expression of AID gene is terminated when the AID gene is located in the reverse direction relative to the promoter; and
(3) Cre recombinase gene is introduced in a manner that enables activation of Cre recombinase by an extracellular stimulus, and the direction of the domain sandwiched between the two loxP domains containing the exogenous AID gene is reversed,
wherein one of the endogenous ASF gene loci is substituted with a promoter having a Tet operator sequence and a gene construct operably linked to an exogenous ASF gene, while the other ASF gene locus is substituted with a promoter and a gene construct functionally bound to a DNA encoding a transcription activating factor having a Tet repressor domain.

In the promoter having a Tet operator sequence, there are no particular limitations on the number of repetitions of the Tet operator sequence so long as the transcription-activating factor having the Tet repressor domain is able to bind to the Tet operator sequence. Examples of promoters having a Tet operator sequence include, but are not limited to, a promoter having a tetracycline-responsive sequence (Tet-responsive sequence has 7 repeating Tet operator sequences) and a TRE promoter (CMV minimum promoter having a Tet-responsive sequence having 7 repeating Tet operator sequences).

In addition, in the promoter having a Tet operator sequence, any promoter can be used as long as it is activated by the binding of a transcriptionactivating factor having a Tet repressor domain (transcription activating factor having a Tet repressor domain and a protein domain having a transcription-activating function). Namely, the type of promoter can be suitably selected according to the type of protein having a transcription activating transcription-activating function.

For example, if the protein having a transcription-activating function is a Herpes simplex virus V16 protein, or a transcription-activating domain of that VP 16 protein, then CMV promoter, CMV minimum promoter, SV40 (simian virus 40) promoter, SV40 minimum promoter, chicken β-actin promoter, and the like, can be used for the promoter (Baim, S. B., Labow, M. A., Levine, A. J., Shenk, T., Proc. Natl. Acad. Sci. USA, 88, 5072-5076 (1991); Kanayama, N., Todo, K., Takahashi, S., Magari, M., Ohmori, N., Nucleic Acids Res., 34, e10 (2006)).

Examples of exogenous ASF genes include genes derived from the same biological species or a biological species different from the biological species from which the endogenous ASF gene is derived. There are no particular limitations on the biological species, and any ASF gene derived from a eukaryote (such as a human, chicken, mouse, cow, horse, pig, sheep, guinea pig, or yeast) can be used. Moreover, a gene having a sequence that completely matches an endogenous ASF gene sequence (or includes a sequence that completely matches the endogenous ASF gene sequence) can also be used as an exogenous ASF gene. In addition, a homologous gene of an endogenous ASF gene may also be used as an exogenous ASF gene.

Any promoter may be used for the promoter located upstream of a DNA encoding a transcription-activating factor having a Tet repressor domain so long as the promoter is activated by an endogenous transcription control factor of the host cells into which the promoter is to be introduced. When using chicken cells for host cells, promoters such as chicken actin promoter and CAG promoter (in which chicken actin promoter is linked to a human cytomegalovirus early enhancer) are included.

The Tet repressor (TetR) is a protein that binds to a Tet operator sequence and which loses the ability to bind to the Tet operator sequence as a result of binding with a tetracycline or an analog thereof. Accordingly, a transcription activating factor having a Tet repressor domain is a transcription activating factor that activates transcription by the binding to a promoter having a Tet operator sequence, and can also be referred to as a transcription-activating factor that loses the ability to bind to a promoter having a Tet operator sequence by binding to a tetracycline or an analog thereof.

A transcription activating factor having a Tet repressor domain refers to a transcription activating factor having a Tet repressor domain and a protein domain having a transcription-activating function. There are no particular limitations on the type of protein having a transcription-activating function so long as it activates a promoter having a Tet operator sequence by binding to that promoter. Namely, the type of protein having a transcription-activating function can be suitably selected based on the type of promoter having a Tet operator sequence. Corresponding examples of promoters and proteins having a transcription-activating function are as described above.

In addition to controlling ASF expression, any type of gene can be used for positive selection so long as it is a gene whose expression is induced by a BCR-mediated signal (and may be an endogenous gene or an externally introduced gene) and that expression allows suppression of cell death induced under various culture conditions. Examples of genes whose transcription is activated by a signal generated as a result of the binding between an antigen and a BCR include, but are not limited to, NFκB and IκB. For example, if various types of drug resistance genes such as neo or puro are located downstream of a gene promoter that is activated by a BCR signal, drug resistance is expressed due to that BCR-mediated signal. Since survival of the cells in the presence of that drug depends on the binding between BCR and the antigen, positive selection by an antigen is made possible in the same manner as in the case of ASF mutant lines.

Namely, the present invention provides a method for selecting B cells that produce a desired antibody, comprising a step where a B cell is introduced with a gene construct containing a promoter of a gene whose transcription is activated by a signal generated as a result of the binding between an antigen and an antibody expressed on B cell surface (B cell antigen receptor on B cell surface), while the promoter is operably linked to a drug resistance gene, where the B cells are cultured with the antigen under conditions in which cell death is induced by that drug, and antibody-producing B cells that bind to the antigen are selected as viable cells.

The "drug" in this method may be any substance so long as it induces cell death.

An innovative antibody production technology employing a culturing system that uses DT40 cells can be established when the positive selection method of the present invention is used in combination with a method which reversibly controls ON/OFF of a mutation function of an antibody gene as described by the present inventors (Kanayama, N., Todo, K., Rieth, M., Ohmori, H., Biochem. Biophys. Res. Commun., 327:70-75 (2005)). In the DT40-SW cells established by the present inventors, expression of activation-induced cytidine deaminase (AID) gene, which governs mutation of an antibody gene, can be reversibly switched ON or OFF by an estrogen derivative supplied from outside. Even if a clone of interest can be isolated from DT40-ASF cells, further mutations are introduced during the course of clone propagation, making it impossible to stably retain useful mutant lines. In order to avoid this problem, it is necessary to terminate the mutating function of the resulting clone of interest. Therefore, as described below, a DT40-SW-ASF cell line, a DT40-SW cell line introduced with an hASF expression controlling means, was also established. By terminating expression of AID in clones selected by positive selection from these DT40-SW-ASF cells, it is possible to obtain genetically stable clones that produce an antibody of interest.

The present invention includes B cells used to select antibody-producing cells by positive selection. Examples of such B cells include the DT40-ASF cells and the aforementioned DT40-SW-ASF cells developed by the present inventors.

Moreover, the present invention provides a method for obtaining a desired antibody which includes the following steps:

(1) selecting B cells that produce a desired antibody according to a method of the present invention, and
(2) obtaining antibodies from the selected B cells.

Antibodies can be obtained by using known methods generally used in the purification of proteins, either alone, or in a suitable combination. For example, antibodies can be separated and purified by suitably selecting an affinity column such as a protein A column, chromatography column, filter, ultrafiltration, salting out or dialysis, or a combination of these methods (Antibodies—A Laboratory Manual, Ed Harlow, David Lane, Cold Spring Harbor Laboratory, 1988).

The antigen binding activity of the obtained antibody can also be retested. A known means can be used for measuring the antigen binding activity of an antibody, examples of which include enzyme-linked immunosorbent assay (ELISA), enzyme immunoassay (EIA), radioimmunoassay (RIA) and fluorescent immunoassay.

In addition, the step of "isolating a DNA encoding an antibody from the B cells" is also included in the aforementioned obtaining of antibodies from B cells. Moreover, isolating a DNA encoding an antibody from B cells and obtaining an antibody from a host transformed with an expression vector containing the DNA is also included in the aforementioned obtaining of antibodies from B cells.

Figure 3:
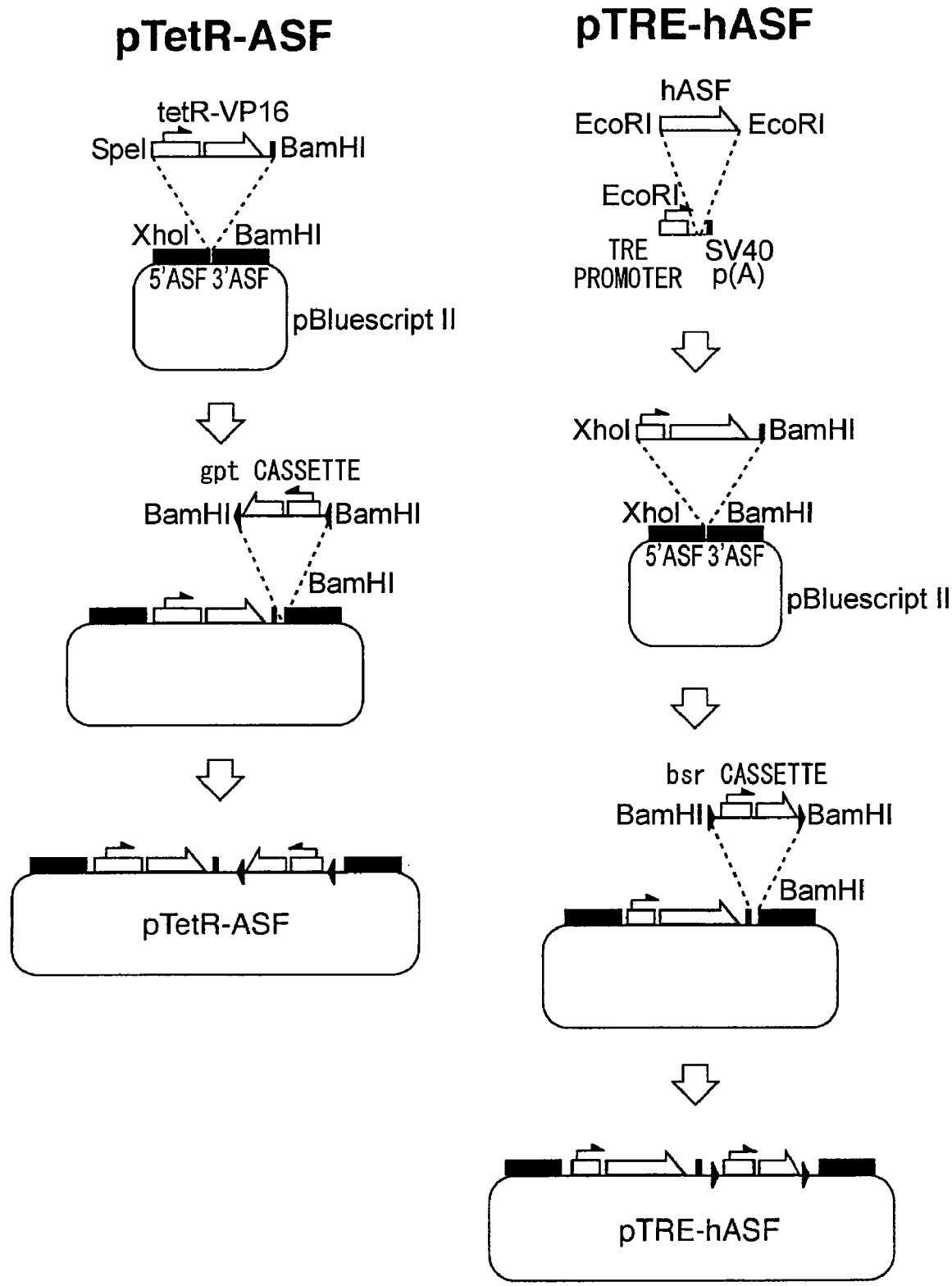
FIG. 3 shows a structural diagram of gene constructs used to prepare DT40 capable of controlling ASF expression.

Expression of DNA encoding an antibody may be carried out by simultaneously transforming host cells in which each DNA encoding an antibody heavy chain (H chain) or light chain (L chain) is incorporated into a separate expression vector. Alternatively, host cells may be transformed by which a DNA encoding H chain or L chain is incorporated into a single expression vector.

Once a DNA encoding an antibody is isolated, a combination of a suitable host and an expression vector can be preferably used when introducing it into a suitable host for producing an antibody. Animal cells, plant cells or fungal cells can be used when eukaryotic cells are used as a host. An expression vector containing a desired antibody gene is introduced into these cells by transformation and the transformed cells are cultured in vitro. A desired antibody can be obtained from a culture of the transformed cells.

Furthermore, transgenic animals can also be preferably used to produce recombinant antibodies in addition to the aforementioned host cells. For example, an antibody gene can be constructed in the form of a fusion gene by in-frame insertion of the gene into a gene encoding a protein produced particularly in breast milk (such as goat β-casein gene).

In addition, the present invention provides an antibody obtained according to the aforementioned method for obtaining desired antibodies. The present invention also provides a variant of the antibody. Examples of antibody variants include chimeric antibodies and humanized antibodies so long as the antibodies prior to variation were non-human animal antibodies.

Chimeric antibodies are antibodies comprising heavy chain and light chain variable regions of a non-human animal antibody and heavy chain and light chain constant regions of a human antibody. A humanized antibody is composed of a complementarity determining region (CDR) of an antibody derived from a non-human animal, a framework region (FR) derived from a human antibody, and a constant (C) region derived from a human antibody.

In addition, examples of antibody variants include low molecular weight antibodies. There are no particular limitations on low molecular weight antibodies so long as they contain an antibody fragment of which a part of the full length antibody is missing but still retains the ability to bind to an antigen. Although there are no particular limitations on an antibody fragment of the present invention so long as it is a part of the full length antibody, it preferably contains a heavy chain variable region (VH) and/or a light chain variable region (VL). Specific examples of low molecular weight antibodies include Fab, Fab', F(ab')2, Fv, scFv (single chain Fv), diabodies and sc(Fv)2 (single chain (Fv)2).

All prior art references cited in the present specification are incorporated herein by reference.

EXAMPLES

The present invention is specifically described by the following Examples, but it is not limited to these examples.

Example 1

Construction of ASF Gene Targeting Construct (pTetR-ASF) Incorporating Tetracycline-Controlled Transcription Activating Factor (tetR-VP16)

An ASF gene targeting construct was constructed for expressing a transcription activating factor to control gene expression under a tetracycline-controlled promoter, and for disrupting one of the loci of endogenous chicken ASF gene (FIG. 2).

A DNA in which tetR-VP16 gene and a rabbit globin poly A addition sequence were arranged in the forward direction downstream of a CAG promoter (in which chicken actin promoter was linked to a human cytomegalovirus early enhancer), and a reverse-oriented guanine phosphoribosyl transferase (gpt) gene expression cassette (expressed under the control of chicken actin promoter, containing an SV40 poly A addition sequence and having a loxP sequence on both ends), were inserted into the first exon part of chicken ASF genomic DNA cloned in a pBluescript II plasmid. Here, the chicken ASF genomic DNA was obtained using PCR method. PCR was carried out with primers designed as indicated below using KOD-Plus (Toyobo Co., Ltd.) and DT40 genomic DNA as the template.

```
5'-end DNA:
Forward primer
5'-TGTGCTGTTAGATCTGCTACAGGCG-3'   (SEQ ID NO: 1)

Reverse primer
5'-TTTCACCTCCGAGGATCCGCCAAGG-3'   (SEQ ID NO: 2)

3'-end DNA:
Forward primer
5'-CGGAGTACAGAGgGATCcTCTCGGG-3'   (SEQ ID NO: 3)

Reverse primer
5'-TTGCCATCAATTAATACAGATGTAC-3'   (SEQ ID NO: 4)
```

After digesting the PCR product with BglII-BamHI for the 5'-end fragment and BamHI-HindIII for the 3'-end fragment, the product was cloned into the BamHI-HindIII site of a pBluescript II vector so as to be arranged in the order of 5'-end and 3'-end. For the CAG promoter and rabbit globin poly A addition sequence, a SpeI-EcoRI fragment and a BglII-BamHI fragment containing the respective sequences in a pCAGGS vector (Niwa, H., et al., 1991, Gene, 108: 193-200) was used. The TetR gene was obtained using PCR method, and an EcoRI-BamHI fragment of the PCR product was used. PCR was carried out with primers designed as indicated below and vector tTA (Wang, J., et al., 1996, Genes & Dev., 10: 1588-2599) as the template.

```
Forward primer
5'-CCCGAATTCATATGTCTAGATTAG-3'     (SEQ ID NO: 5)

Reverse primer
5'-CGCGGATCCTACCCACCGTACTCGTC-3'   (SEQ ID NO: 6)
```

For the gpt gene expression cassette, a BamHI fragment containing a gpt gene of pΨVdel1-25 (Arakawa, H. et al., 2004, PLoS Biol., 2: 967-974) was used. A DNA (having a SpeI site and BamHI site on both ends), in which a TetR gene, and a rabbit globin poly A addition sequence were arranged in the forward direction downstream of a CAG promoter between XhoI-BamHI site that is located between the 5'-end fragment and the 3'-end fragment of a chicken ASF in a vector cloned with chicken ASF, and a gpt expression cassette were incorporated in that order (FIG. 3).

Example 2

Construction of a Construct (pTRE-hASF) for Targeting ASF Gene Locus Capable of Expressing Human ASF Gene only in the Absence of Tetracycline A construct which is capable of expressing human ASF gene under conditions where tetracycline is absent and which is used for the disruption of one of the gene loci of the endogenous chicken ASF gene was constructed (FIG. 3).

A DNA in which human ASF gene and SV40 poly A addition sequence were arranged in the forward direction downstream of a TRE promoter (CMV minimum promoter having a Tet-responsive sequence which has 7 repeating tet-O sequences), and a blastocydine S resistance gene (bsr) expression cassette (expressed under the control of chicken actin promoter, containing an SV40 poly A addition sequence, and having a loxP sequence on both ends) were inserted into the first exon part of the chicken ASF genomic DNA cloned in a pBluescript II plasmid.

For the chicken ASF genomic DNA cloned in the pBluescript II vector, the chicken ASF genomic DNA used in Example 1 was used. An XhoI-HindIII fragment containing a TRE sequence of Puro-ASF (Wang, J., et al., 1996, Genes & Dev., 10, 1588-2599) was used for the TRE promoter, while that introduced with a BamHI site by linking a linker to the SpeI side of an HindIII-SpeI fragment containing an SV40 poly A sequence of pExpress (Arakawa, et al., 2001, BMC Biotechnol., 1:7) was used for the SV40 poly A addition sequence. An EcoRI fragment containing human ASF sequence of Puro-ASF was used for human ASF gene. The TRE fragment and the SV40 poly A addition sequence were bound to a HindIII site, and the ASF gene fragment was incorporated into an EcoRI site between the TRE sequence and the SV40 poly A addition sequence to obtain a human ASF expression cassette. A BamHI fragment of pLoxBsr (Arakawa, H., et al., 2001, BMC Biotechnol., 1:7) was used for the bsr expression cassette. The human ASF expression cassette (having an XhoI site and BamHI site on both ends) and the bsr expression cassette were incorporated in that order between the XhoI-BamHI site that is between the 5'-end fragment and the 3'-end fragment of the chicken ASF in a vector cloned with chicken ASF (FIG. 3).

Example 3

Preparation of Cells Enabling Positive Selection using B Cell Antigen Receptor Signals resulting from the regulation of ASF Expression with Tetracycline (DT40-ASF and DT40-SW-ASF)

One of the endogenous ASF gene loci of wild DT40 cell line or DT40-SF cell line uniquely established by the present inventors (a mutant cell line enabling ON/OFF control of its antibody mutation function by reversibly switching the expression of AID gene that governs the mutation function, details of which are described in Kanayama, N., Todo, K., Reth, M., Ohmori, H., Biochem. Biophys. Res. Commun., 327:70-75 (2005)) was substituted with a human ASF (hASF) gene construct linked to a TRE promoter. The other ASF gene locus, on the other hand, was substituted with a transcription-factor (tetR-VP16, indicated by the open circle inside the diagram of B cells) expression construct that promotes transcription by binding to a tetracycline responsive sequence to produce cell lines DT40-ASF and DT40-SW-ASF (FIG. 4B). tetR-VP16 is a gene construct that links a tetR (tet repressor) having the ability to bind to tet-O in the absence of tetracycline or analogs thereof (e.g., Dox, indicated by vertical bars in FIG. 4B) with a transcription activating domain of Herpes simplex virus VP16 protein, which can be produced according to the description of Wang, J., Takagaki, Y., Manley, J. L., Genes Dev., 10:2588-2599 (1996).

(1) Cell Culturing

DT40 cells and a gene-introduced cell line thereof were cultured in RPMI1640 medium (ICN Biomedicals) containing 10% fetal bovine serum, 1% chicken serum, 50 µM 2-mercaptoethanol, 2 mM glutamine, 1 mM pyruvic acid, 100 µg/ml penicillin G and 50 µg/ml streptomycin in a $CO_2$ incubator at 37° C., with 5% $CO_2$.

(2) Gene Introduction into DT40 Cells

Gene introduction into DT40 cells was carried out by adding 15 µg of linear plasmid DNA into $5 \times 10^6$ cells and then performing electroporation using Gene Pulser Xcell (Bio-Rad Laboratories) under conditions of 550 V and 2 µF.

(3) Preparation of Cells Capable of Controlling Expression of ASF

A pTetR-ASF construct made into a linear form using ApaLI was introduced into the DT40-SW cells. At that time, selection was carried out by adding mycophenolic acid to the medium to a concentration of 25 µg/ml. Clones in which the pTetR-ASF construct had been subjected to targeted homologous recombination at one of the ASF gene loci could be obtained among those mycophenolic acid resistant clones (DT40-ASF+/−cell line). Moreover, a pTRE-hASF construct was made into a linear form using ApaLI was introduced into the above DT40-ASF+/−cells under the same conditions. At that time, selection was carried out by adding blastocydine S to the medium to a concentration of 50 µg/ml. Clones in which the pTRE-hASF construct was subjected to targeted homologous recombination at the other remaining ASF gene locus could be obtained among those blastocydine S resistant clones. These cells were used as cells capable of controlling expression of ASF with tetracycline (DT40-ASF and DT40-SW-ASF cell lines).

Since hASF is expressed in these cell lines in the absence of tetracycline as a result of tetR-VP16 binding to a promoter having tet-O, the cells proliferate normally. On the other hand, when tetracycline or a derivative thereof in the form of doxycycline (Dox) is added, the cells cannot survive because the expression of hASF is terminated due to Dox binding to tetR-VP16 causing tet-O to be released from tetR-VP16. The DT40-ASF and DT40-SW-ASF cell lines capable of controlling expression of hASF obtained in this manner can be used to select desired antibody-producing cells as indicated in the following Examples 4 and 5. In particular, the use of DT40-SW-ASF cell line is extremely useful since it enables a desired clone to be proliferated in a genetically stable form by terminating the mutation function by turning OFF the AID expression of the obtained cells when the antigen-specific clone is selected in the presence of antigen and Dox.

The DT40-SW cell line has cells which have been altered from chicken B cell DT40 cell line, in which, subsequent to the disruption of the original AID gene, a modified AID (activation-induced cytidine deaminase) gene construct, which is modified to a form that enables ON/OFF regulation of expression by an extracellular stimulus, is introduced at the original AID site. AID is an enzyme that has an essential role in somatic hypermutation, and mutations do not occur unless AID functions. DT40 cells constitutively express AID, and spontaneously introduce mutations into the variable regions of antibody genes during culture. In the DT40-SW cell line, the AID gene is sandwiched between two loxP sequences in mutually opposite directions, and when Cre recombinase (Cre) is activated by an extracellular stimulus, reverting of the direction of the AID gene enables the conversion of the expression of the AID gene controlled by a promoter located upstream of the domain positioned between the two loxP sequences to be switched from promotion (ON) to termination (OFF) or from OFF to ON. Namely, when the AID gene is oriented in the forward direction relative to the promoter, expression is maintained in the ON state. However, when the AID gene is oriented in the reverse direction relative to the promoter, the expression thereof is maintained in the OFF state.

In order to obtain DT40-SW cell line, cells are first altered by functionally disrupting endogenous AID gene of cells derived from any vertebrate capable of expressing endogenous AID gene, so that production of AID protein by expression of endogenous AID gene would not occur. One of alleles of endogenous AID gene are subjected to gene disruption (knockout) by producing an AID gene targeting vector according to the normal procedure. At the other allele, on the other hand, an AID gene targeting vector containing a DNA construct that contains a gene encoding exogenous AID constructed so as to allow inversion of the direction thereof by Cre recombinase is produced to cause homologous recombination, thereby enabling disruption of the endogenous AID gene and the production of cells capable of controlling expression of an exogenous AID gene. The exogenous AID gene constructed so as to allow inversion of the direction thereof by Cre recombinase is mutually positioned between two loxP sequences in opposite directions. Moreover, a promoter is present at the upstream side of the domain positioned between the two loxP sequences that functions in the subject animal cells, and a target vector is designed so that the promoter is also inserted into the genome by homologous recombination. Thus, by incorporating an exogenous AID gene constructed so as to allow inversion of the direction thereof by Cre recombinase in the cell genome, expression of AID gene is induced by the promoter when the exogenous AID gene is located in the forward direction relative to that promoter. It goes without saying that expression of AID gene does not occur when the AID gene is located in the reverse direction relative to the promoter. Those skilled in the art can postulate and select various promoters to be used as a suitable promoter, examples of which include β-actin promoter, immunoglobulin promoter, cytomegalovirus promoter and CAG promoter. As a result of such a DNA construct containing exogenous AID gene being present in a genome, when Cre recombinase is activated in the cells, it acts on loxP, and thereby causes inversion of the domain positioned between the two loxP (namely, the orientation of the AID gene changes from the reverse to the forward direction or from the forward to the reverse direction). As a result, expression of AID gene is switched from ON to OFF or from OFF to ON. Cre recombinase gene is preferably introduced into the cells in such a manner that activation of Cre recombinase is induced by an extracellular stimulus. For example, a DNA construct is preferably introduced into the cells in which a gene encoding a protein containing an estrogen receptor or the estrogen binding domain and Cre recombinase cDNA are linked in-frame in a manner such that Cre recombinase can be expressed as a fusion protein with a protein containing estrogen receptor or the estrogen binding domain. In this case, when an estrogen derivative stimulus is given to the cells, activation of Cre recombinase is induced. Thus, Cre recombinase is activated only when an estrogen derivative is given extracellulary, resulting in the inversion of the domain containing the AID gene, positioned between the loxP sequences.

Figure 5:
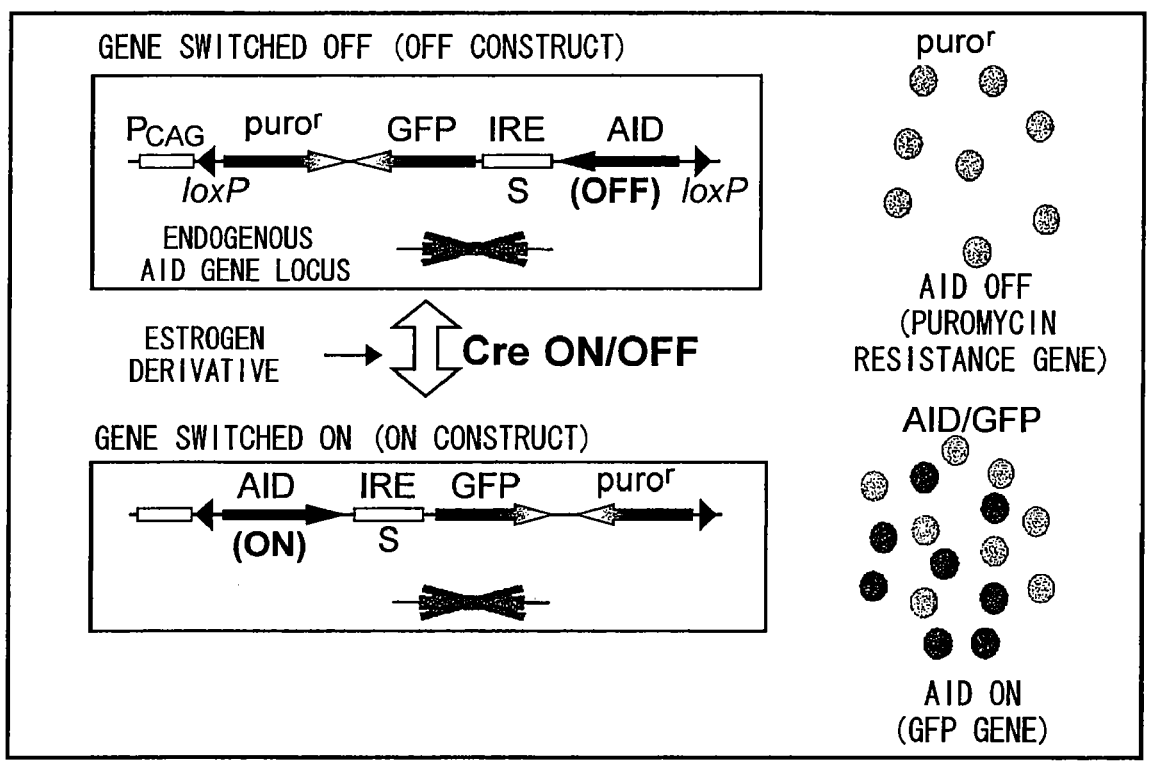
FIG. 5 shows a construct for producing the DT40-SW cell line. This drawing represents ON/OFF control of the expression of AID (activation-induced cytidine deaminase) in DT40 cells by a Cre/loxP system. The native AID gene of the DT40 cells is disrupted by gene targeting. A separately cloned AID gene is introduced into one of the AID loci between two loxP's, and the direction of insertion is reversed as a result of Cre recombinase activity being switched ON by an extracellular stimulus, resulting in ON/OFF of AID expression. When OFF, useful mutations can be fixed and isolated. In addition, when AID is again switched ON, mutations resume, thereby enabling further accumulation of useful mutations.

Namely, the DT40-SW cell line features vertebrate cells that enable induction or termination of activation-induced cytidine deaminase (AID) expression, as a result of induction of exogenous Cre recombinase gene expression by an extracellular stimulus, and inversion of orientation of exogenous AID gene by the expressed Cre recombinase, wherein the cells are characteristic in that:

(1) endogenous AID gene is functionally disrupted, and no AID protein is produced due to the expression of endogenous AID gene;

(2) has an exogenous AID gene positioned in between two loxP sequences that are in opposite directions and a promoter capable of functioning in animal cells is present upstream of the domain positioned in between those two loxP sequences, in which promoter-induced AID gene expression is possible when the AID gene is located in the forward direction relative to the promoter, while expression of AID gene terminates when the AID gene is located in the reverse direction relative to the promoter; and (3) Cre recombinase gene is introduced in such a manner that enables activation of Cre recombinase by an extracellular stimulus, and the direction of the domain containing the exogenous AID gene, positioned between the two loxP domains, is reverted by the activation of Cre recombinase. In addition, these cells are such that the aforementioned Cre recombinase gene is present in a way that Cre recombinase is expressed as a fusion protein with an estrogen receptor, in which the aforementioned extracellular stimulus is a stimulus that is due to an estrogen or a derivative thereof, and intracellular Cre recombinase activation is induced as a result of stimulating cells extracellulary with estrogen or a derivative thereof. Moreover, in these cells, a marker gene heading the same direction as the AID gene is further contained in the domain positioned in between the two loxP sequences. When the AID gene as well as the marker gene is located in the forward direction relative to the promoter, the marker gene is expressed, and cells capable of expressing the AID gene as a result of the AID gene being located in the forward direction relative to the promoter can be selected based on that marker. Moreover, these cells further contain a marker gene heading the opposite direction of the AID gene in the domain positioned between the two loxP sequences. When the AID gene is located in the reverse direction relative to the promoter but the marker gene is located in the forward direction, the marker gene is expressed and cells that are unable to express the AID gene because the AID gene is located in the reverse direction relative to the promoter, can be selected by the marker gene. Moreover, these cells also include cells in which the marker gene heading the opposite direction of the AID gene in the domain positioned between the above mentioned two loxP sequences is a puromycin resistance gene, and the marker gene heading the same direction as the AID gene is a GFP gene. FIG. 5 shows constructs for producing DT40-SW cell lines.

Example 4

Survival of Doxycycline-Treated DT40-ASF Cells due to the Binding of Antigen to BCR Cells established according to the method of Wang, et al. (Wang, J., Takagaki, Y., Manley, J. L., Genes Dev., 10:2588-2599 (1996)) or DT40-ASF cells produced according to the method described in Example 3 were used for the DT40-ASF cells.

Figure 6:
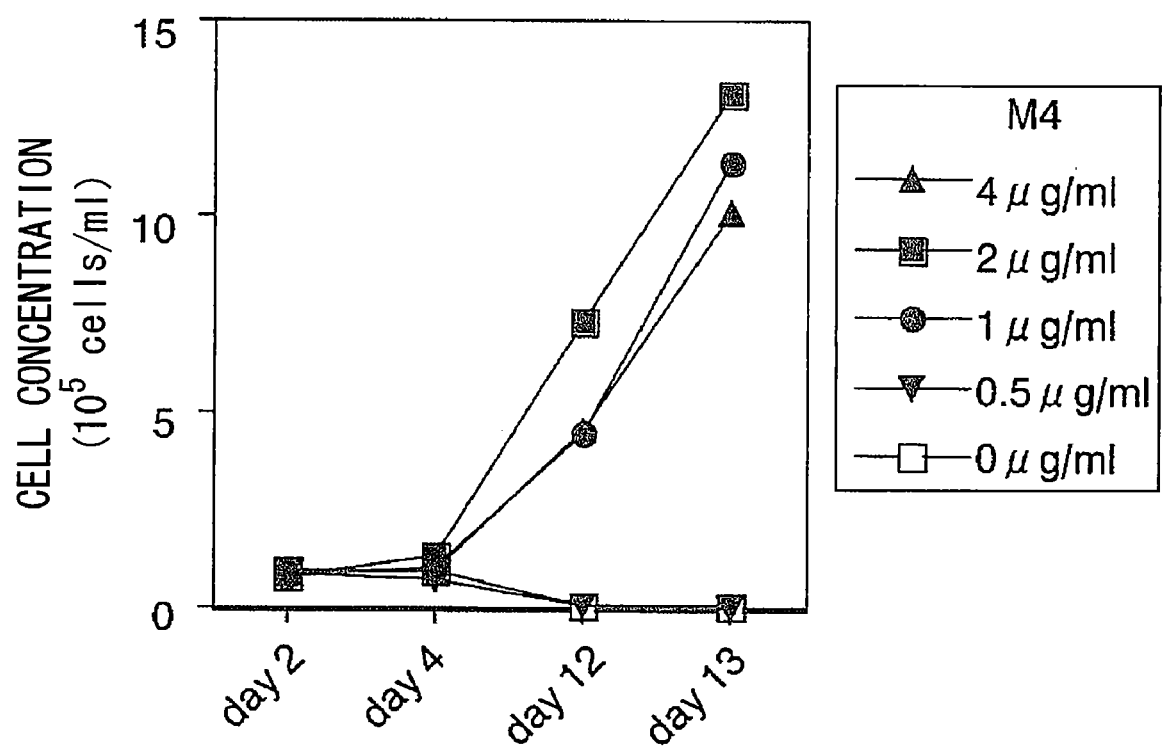
FIG. 6 shows suppression of cell death by DT40-ASF in the presence of doxycycline resulting from the binding between anti-IgM monoclonal antibody (M4) and BCR. Vertical axis: Proliferation of DT40-ASF cells. Horizontal axis: Culture Duration after adding anti-IgM antibody (M4).

$1 \times 10^6$ DT40-ASF cells were cultured in 1 ml of RPMI-1640 medium. When a tetracycline derivative, doxycycline (Dox), was added at 10 ng/ml at the start of culture, nearly all the cells died by the 4$^{th}$ day of culture (FIG. 6). This was due to the fact that ASF expression was terminated by doxycycline. When antibody M4 (mouse-derived anti-chicken IgM monoclonal antibody), which binds to and crosslinks with BCR, was added in advance to the medium at 1 µg/ml or more, recovery of cell proliferation was observed on day 12 of culture. Since this phenomenon was observed M4 concentration-dependently but not observed in the absence of M4, those cells that should have died due to the addition of doxycycline are thought to have survived due to the binding of antigen to BCR.

The results of this experiment show that, in DT40-ASF cells, cell death occurring due to the termination of ASF expression is avoided if binding of antigen to BCR takes place. This suggests that when a specific antigen binds to BCR, positive selection of antigen-specific cells is possible since only those cells specific for the antigen are expected to survive. The following Example 5 shows that this is possible.

Example 5

Positive Selection of Antigen-Specific DT40 Cells in the Presence of Antigen

Figure 7:
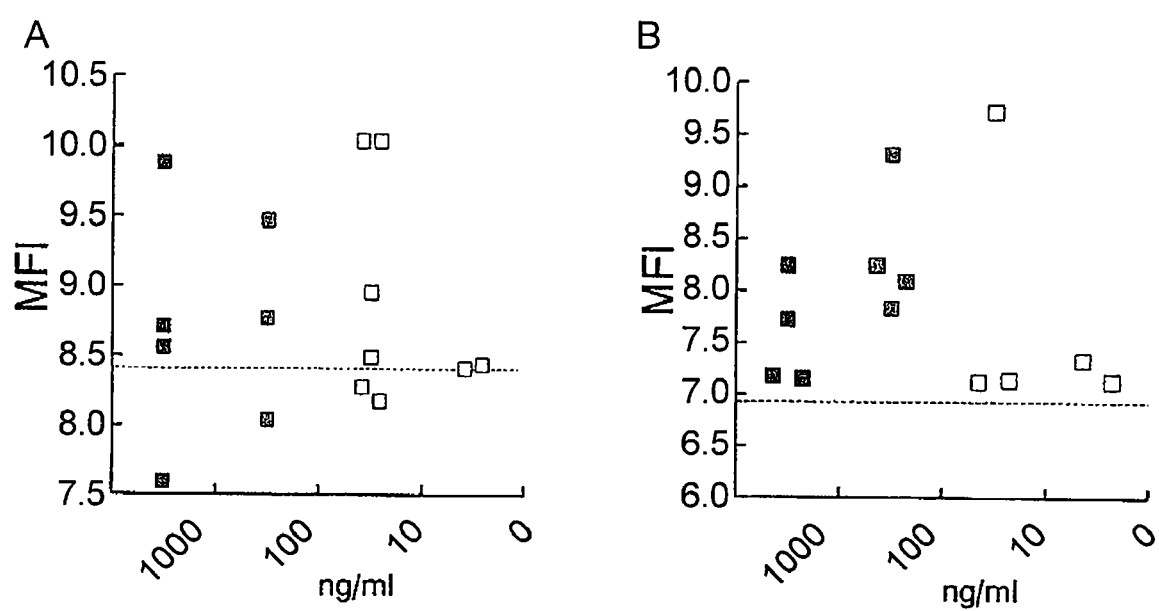
FIG. 7 shows the results of positive selection of antigen-specific clones from a DT40-ASF cell population using an antigen. A indicates the results of selecting against NP-BSA while B indicates the results of selecting against pNP-BSA. Vertical axes of FIGS. 7A and 7B: Mean fluorescence intensity (MFI) of antigens bound to isolated clones. MFI values were obtained by reacting each clone with biotinated NP-BSA (FIG. 7A) or pNP-BSA (FIG. 7B) followed by staining with FITC-streptavidin and measuring the fluorescence intensity of FITC using a flow cytometer. Horizontal axes of FIGS. 7A and 7B: Concentration of each antigen used for positive selection.

A study was conducted as to whether or not positive selection of DT40-ASF cells expressing BCR that specifically bind with a 4-hydroxy-3-nitrophenylacetyl group (NP) or p-nitrophenylacetyl group (pNP) is possible in bovine serum albumin (BSA) using NP or pNP as hapten, and NP-BSA or pNP-BSA as a selection antigen, in which approximately 20 NP or pNP was covalently bound to a molecule of BSA. 0.2 ml of medium containing $1 \times 10^3$ DT40-ASF cells were dispensed into each well of a 96-well culture plate followed by the addition of NP-BSA or pNP-BSA to a concentration of 10 to 1000 ng/ml. Moreover, doxycycline was added to each well to a concentration of 10 ng/ml, and then cultured for 10 days. A plate subjected to the same conditions but not containing selection antigen was used as a control. As shown in FIG. 7, an apparent proliferation of a large number of colonies was confirmed in the presence of NP-BSA and pNP-BSA as compared to the control. When isolated colonies were grown and their binding ability was evaluated against each antigen using flow cytometry, colonies with increased mean fluorescence intensity (MFI) was observed in comparison with cells prior to selection. MIF is measured subsequent to the staining by a fluorescent-labeled antigen. Thus, an ASF expression control mechanism introduced into DT40-ASF cells can be used for positive selection of antigen-specific clones. Several clones were selected from a total of up to $10^5$ cells, which is considered a reasonable selection efficiency considering the incidence of antigen-specific clones.

Example 6

Figure 8:
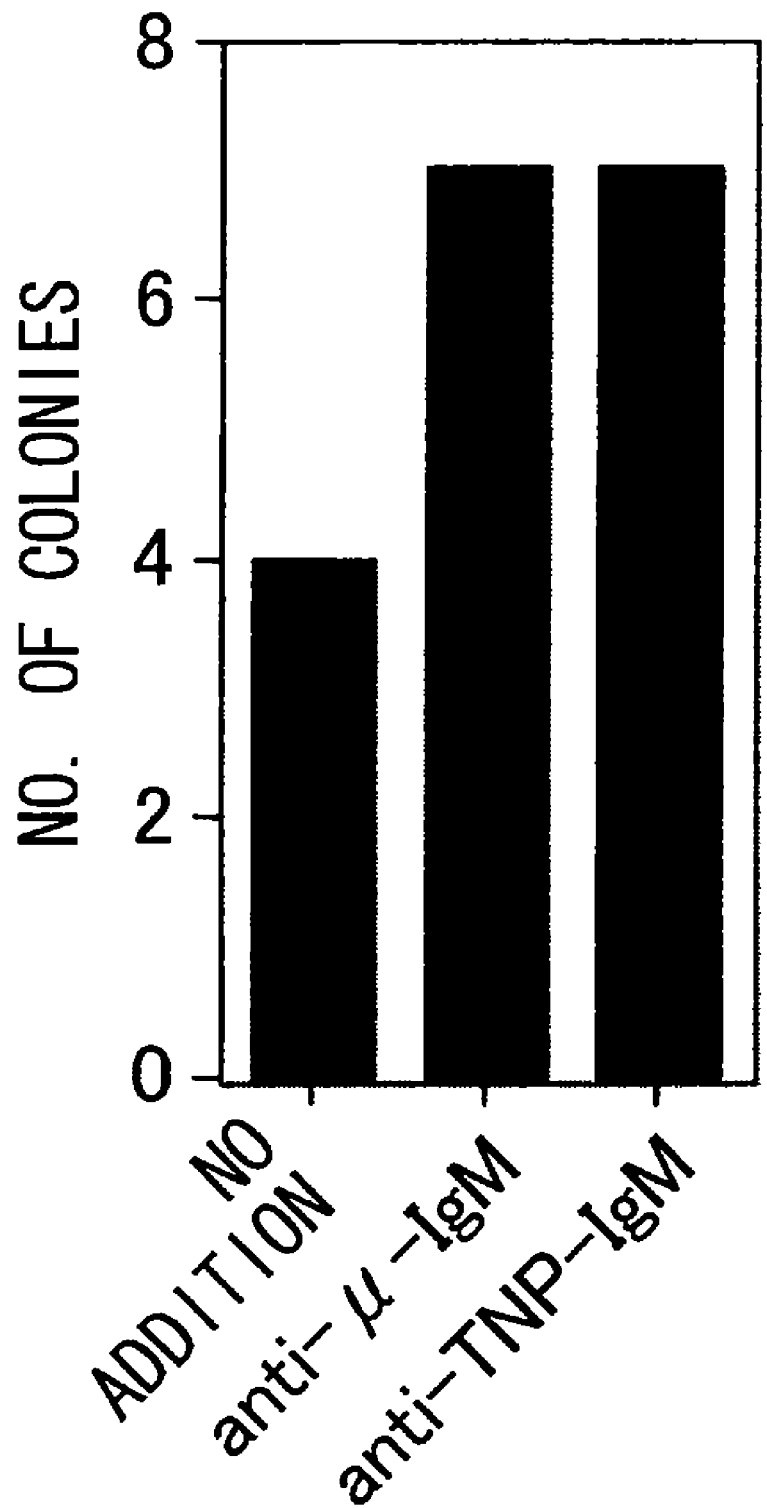
FIG. 8 shows a comparison of the numbers of colonies that appear for surface-IgM-specific IgM antibody and non-specific IgM antibody.

Importance of Antigen Recognition by BCR on DT40-ASF in the Positive Selection Process $10^5$ DT40-ASF cells were suspended in a medium containing 100 ng/ml doxycycline (dox) and 2 µg/ml mouse derived anti-µ IgM antibody or anti-TNP IgM antibody and then dispensed into a 96-well plate and cultured. The number of colonies that appeared after 2 weeks were counted (TNP is the abbreviation for 2,4,6-trinitrophenyl). The colony appearance rates were roughly the same for both anti-µ IgM having the ability to crosslink surface IgM and anti-TNP IgM which does not have that ability. In both cases, larger numbers of colonies appeared as compared to no addition (FIG. 8). This suggests that it is important for both IgM antibodies to be recognized by surface antibodies (BCR) of DT40 cells as IgM protein antigens, and that the anti-IgM crosslinking BCR appearing on the surface of DT40-ASF does not lead to a generation of a suitable survival signal for the cells.

Example 7

Construction of Constructs for Disrupting Antibody Light Chain Gene (pIgL-KO)

Figure 9:
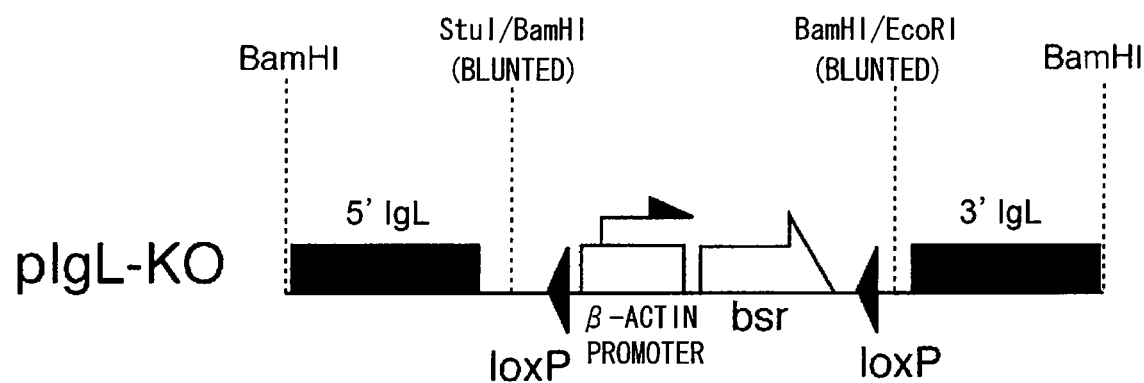
FIG. 9 shows a structural diagram of a construct for disrupting antibody light chain gene.

An antibody light chain gene targeting construct having a blastocydine S resistance gene was constructed to disrupt antibody light chain gene of DT40 cells and to create a cell surface with no BCR (FIG. 9).

A bsr expression cassette was inserted into the variable region part of the chicken antibody light chain genomic DNA cloned into pBluescript II.

A fragment cloned to pCR-Blunt (Kanayama, N., Todo, K., Takahashi, S., Magari, M., Ohmori, H., 2006, Nucleic Acids Res., 34: e10) was used for the chicken antibody light chain genomic DNA. A BamHI fragment containing bsr of pLox-Bsr was used for the bsr expression cassette. Fragments of the 5' and 3' ends of chicken antibody light chain DNA cloned into pCR-Blunt were introduced into pBluescript II so as to be aligned in the order of the 5' end and 3' end, respectively, which were then digested with StuI-EcoRI to delete sites containing an antibody variable region and to blunt the digested ends. To this, a blunted bsr expression cassette was incorporated to make an antibody gene targeting construct.

Example 8

Figure 10:
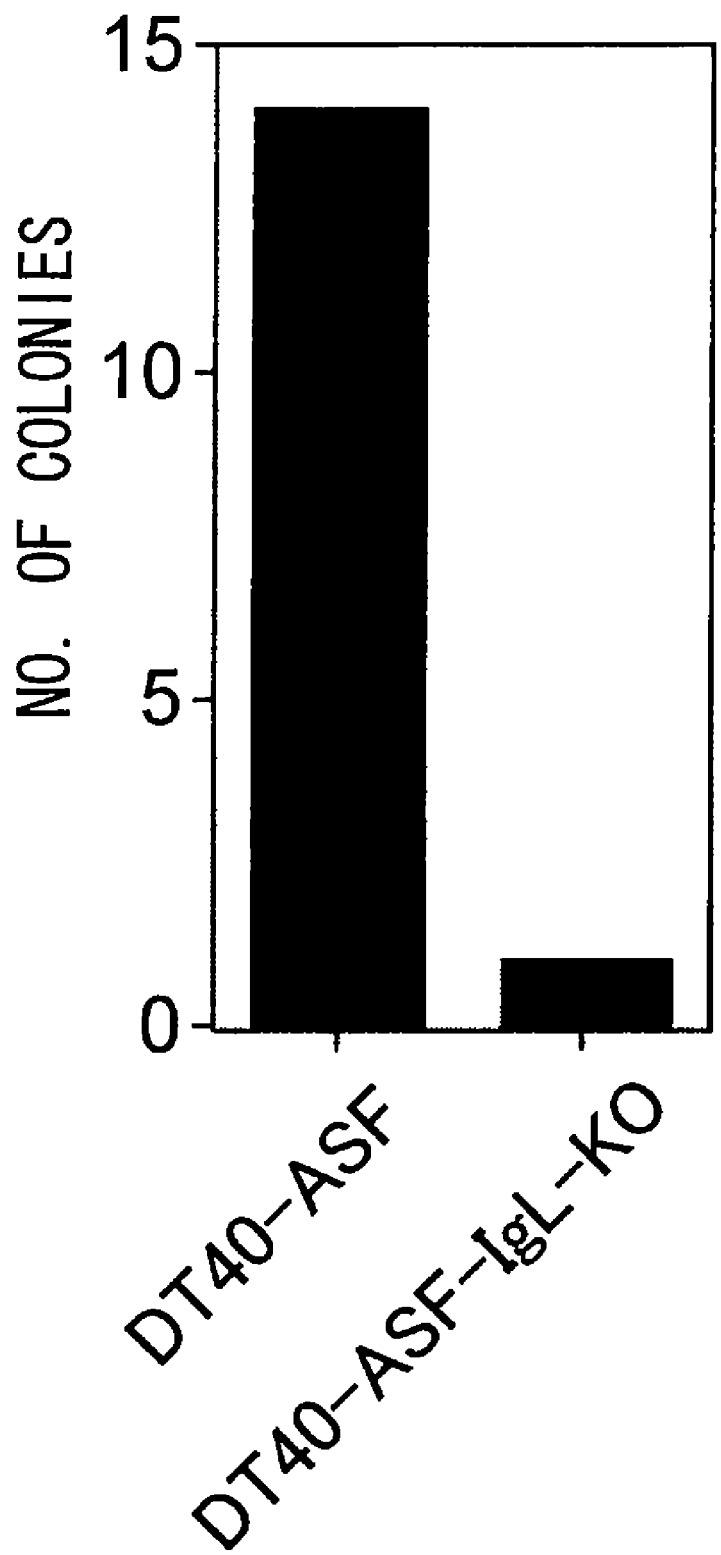
FIG. 10 is a graph verifying the need of DT40-ASF cell surface antibodies in positive selection.

Necessity of BCR Expression on DT40 Cells during the Process of Positive Selection by an Antigen Cells in which an antibody L chain gene of DT40-ASF cells was disrupted by gene targeting were produced (DT40-ASF-IgL-KO). $10^6$ cells each of DT40-ASF and DT40-ASF-IgL-KO cells were cultured for 2 weeks by dispensing into two 96-well plates in the presence of 100 ng/ml of dox. Fourteen DT40-ASF colonies appeared whereas, only one DT40-ASF-IgL-KO colony was observed (FIG. 10). Since serum was added to the medium as a medium component, various antigens are believed to stimulate DT40 surface antibodies. Therefore, to a certain degree, colonies are thought to appear even if an antigen is intentionally not added from the outside. Since L chain is not synthesized in DT40-ASF-IgL-KO cells, IgM is not expressed on the surface (separately confirmed by FACS, data not shown). The significant decrease in the number of colonies appearing in the presence of dox in the case of IgL-KO cells suggests that the entry of signals from BCR is important for positive selection of antigen-specific antibodies.

Industrial Applicability

Until now, the only ways to select a specific clone to an antigen from a population of cultured B cells were random screening and the so-called panning method that utilizes physical adsorption to a solid phase to which an antigen is bound. In these methods, however, it is difficult to isolate cells having an extremely low incidence and it is necessary to repeat the procedure to concentrate the desired clone. In addition, the risk of overlooking important clones cannot be ruled out completely.

In contrast, in the positive selection method of the present invention, selection is possible regardless of the low clone frequency since the selection is basically carried out in the same manner as the selection in a living body, and is particularly effective for concentrating a desired clone in early cultures. In the present invention, the inventors succeeded in establishing conditions that enable survival of only cells bound to antigen following reaction of the antigen with a B cell population. Cells that are not bound to the antigen die, and these conditions were used to establish a method for positive selection. According to this method, even B cell clones having an extremely low incidence can be isolated.

A combination of this method with the method for reversibly controlling the ON/OFF of the mutation function of antibody genes described in a paper of the present inventors (Kanayama, N., Todo, K., Reth, M., Ohmori, H., Biochem. Biophys. Res. Commun., 327:70-75 (2005)) enables the establishment of an innovative antibody production technology using a culture system that uses DT40 cells.

The invention claimed is:

1. A method for selecting B cells that produce a desired antibody, comprising:
   a) culturing B cells with a drug at concentrations sufficient to terminate expression of an exogenous ASF gene;
   b) culturing the B cells with an antigen; and
   c) selecting antibody-producing B cells that bind the antigen as viable cells;
   wherein the B cells comprise:
      i) a functionally disrupted endogenous ASF gene,
      ii) a gene construct having a drug-suppressable promoter operably linked
      to the exogenous ASF gene, and
   wherein cell death is induced by terminated expression of the exogenous ASF gene in the presence of the drug, and cell death is suppressed by a survival signal generated as a result of binding between an antigen and an antibody expressed on the B cell surface (B cell antigen receptor on the B cell surface).

2. A method for selecting B cells that produce a desired antibody, comprising:
   a) culturing B cells with an antigen under conditions in which cell death is induced by tetracycline or an analog thereof, and
   b) selecting antibody-producing B cells that bind with the antigen as viable cells; wherein the B cells comprise:
      (i) a first endogenous ASF gene locus substituted with a gene construct containing a promoter having a Tet operator sequence operably linked to an exogenous ASF gene; and
      (ii) a second endogenous ASF gene locus substituted with a gene construct containing a promoter operably linked to a DNA encoding a transcription activating factor having a Tet repressor domain;
   wherein cell death is induced by terminated expression of the exogenous ASF gene in the presence of tetracycline or an analog thereof, and cell death is suppressed by a survival signal generated as a result of binding between an antigen and an antibody expressed on B cell surface (B cell antigen receptor on the B cell surface).

3. A method for selecting B cells that produce a desired antibody, comprising:
   a) culturing B cells with Tetracycline or an analog thereof at concentrations sufficient to terminate expression of an exogenous ASF gene;
   b) culturing the B cells with an antigen; and
   c) selecting antibody-producing B cells that bind the antigen as viable cells, wherein the B cells comprise:
      (i) a gene construct in which a promoter having a Tet operator sequence and an exogenous ASF gene are operably linked; and
      (ii) a gene construct in which a promoter and a DNA encoding a transcription activating factor having a Tet repressor domain are operably linked, and
   wherein cell death is induced by terminated expression of the exogenous ASF gene in the presence of Tetracycline or an analog thereof, and cell death is suppressed by a survival signal generated as a result of binding between an antigen and an antibody expressed on the B cell surface (B cell antigen receptor on the B cell surface).

4. The method of claim 1, wherein the B cells are from a chicken B cell line.

5. The method of claim 1, wherein the B cells are from the chicken B cell line DT40.

6. The method of claim 1, wherein the B cells are from the chicken B cell line DT40, and the exogenous ASF gene is a human ASF gene.

7. A method for obtaining a desired antibody, comprising the steps of:
   (i) selecting B cells producing a desired antibody according to the method of any one of claim 4, 5, 6, 1 or 2; and
   (ii) obtaining the antibody from the selected B cells.

8. A B cell in which expression of an exogenous Cre recombinase gene is induced by an extracellular stimulus, and expression of activation-induced cytidine deaminase (AID) can be induced or terminated by the expressed Cre recombinase, the B cell comprising:
   (i) a functionally disrupted endogenous AID gene;
   (ii) an exogenous AID gene sandwiched between two loxP sequences in mutually opposite directions, and a first promoter able to function in the cells is present upstream of the exogenous AID gene sandwiched between the two loxP sequences, in which promoter-mediated expression of AID gene is induced when the AID gene is located in the forward direction relative to the promoter, while expression of AID gene is terminated when the AID gene is located in the reverse direction relative to the promoter; and
   (iii) a Cre recombinase gene encoding a Cre recombinase capable of activation by an extracellular stimulus, wherein activation of Cre recombinase results in reversal of the direction of the exogenous AID gene sandwiched between the two loxP sequences;
   wherein the B cell further comprises one endogenous ASF gene locus substituted with a gene construct containing a second promoter having a Tet operator sequence operably linked to an exogenous ASF gene, and the other ASF gene locus substituted with a gene construct containing a third promoter operably linked to a DNA encoding a transcription activating factor having a Tet repressor domain.

9. The cell of claim 8, wherein the B cell is from a chicken B cell line.

10. The B cell of claim 8, wherein the B cell is from the chicken B cell line DT40.

11. The B cell of claim 8, wherein the B cell is from the chicken B cell line DT40 and the exogenous ASF gene is a human ASF gene.

12. The method of claim 1, wherein the drug is tetracycline or an analog thereof.

13. The method of claim 1 or 2, wherein the B cells further comprise:
   i) a functionally disrupted endogenous activation-induced cytidine deaminase (AID) gene;
   ii) an exogenous AID gene sandwiched between two loxP sequences in mutually opposite directions;
   iii) a promoter capable of functioning in the cells is operably linked to the exogenous AID gene sandwiched by the two loxP sequences, in which promoter-mediated expression of the AID gene is induced when the AID gene is located in the forward direction relative to the promoter, while expression of the AID gene is terminated when the AID gene is located in the reverse direction relative to the promoter; and
   (iv) a Cre recombinase gene encoding a Cre recombinase capable of activation by an extracellular stimulus, wherein activation of Cre recombinase results in reversal of the direction of the exogenous AID gene sandwiched between the two loxP sequences.

14. The method of claim 2, wherein the B cells are from a chicken B cell line.

15. The method of claim 2, wherein the B cells are from the chicken B cell line DT40.

16. The method of claim 2, wherein the B cells are from the chicken B cell line DT40, and the exogenous ASF gene is a human ASF gene.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 1
tgtgctgtta gatctgctac aggcg                                         25

<210> SEQ ID NO 2
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 2
tttcacctcc gaggatccgc caagg                                         25

<210> SEQ ID NO 3
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 3
cggagtacag agggatcctc tcggg                                         25

<210> SEQ ID NO 4
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 4
ttgccatcaa ttaatacaga tgtac                                         25

<210> SEQ ID NO 5
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 5
cccgaattca tatgtctaga ttag                                          24

<210> SEQ ID NO 6
<211> LENGTH: 26
<212> TYPE: DNA
<213> ORGANISM: Artificial
<220> FEATURE:
<223> OTHER INFORMATION: An artificially synthesized primer sequence

<400> SEQUENCE: 6
cgcggatcct acccaccgta ctcgtc                                        26
```